United States Patent [19]
Canavesi et al.

[11] 4,377,491
[45] Mar. 22, 1983

[54] OXYCHLORINATION CATALYST PRECURSOR AND PROCESS FOR ITS PREPARATION

[75] Inventors: Roberto Canavesi, Arese; Roberto Ghezzi, Cusano Milanino; Vittorio Tagliabue, Limbiate, all of Italy

[73] Assignee: Euteco Impianti S.p.A., Milan, Italy

[21] Appl. No.: 345,465

[22] Filed: Jan. 3, 1982

[30] Foreign Application Priority Data

Feb. 12, 1981 [IT] Italy .................................. 19689 A/81
Aug. 17, 1981 [IT] Italy .................................. 68126 A/81

[51] Int. Cl.³ ............................................. B01J 27/10
[52] U.S. Cl. .................................... 252/441; 252/442; 570/243
[58] Field of Search ................................. 252/441, 442

[56] References Cited

U.S. PATENT DOCUMENTS 3,148,222 9/1964 Penner et al. .................... 252/442 X
3,267,161 8/1966 Ukaji et al. ....................... 252/441 X
3,461,084 8/1969 Li ......................................... 252/441
3,483,136 12/1969 van der Plas et al. ............... 252/441
3,709,950 1/1973 Baker et al. ....................... 252/442 X
4,069,170 1/1978 Blake et al. ........................... 252/441

*Primary Examiner*—Patrick Garvin
*Attorney, Agent, or Firm*—Birch, Stewart, Kolasch & Birch

[57] ABSTRACT

An oxychlorination catalyst precursor is described which is constituted by porous microspheroidal alumina particles impregnated with 3 to 7% by weight of cupric chloride (expressed in terms of the copper metal) and containing from 0.5 to 2% by weight of water, in which the copper is uniformly distributed over the entire surface area of the particles with a degree of non-uniformity not greater than ±7%.

A process for the preparation of such a catalyst precursor is also described.

The precursor is activated to give a catalyst which is readily fluidizable and which enables the oxychlorination of ethylene to dichloroethane to be carried out with high activity and selectivity values.

5 Claims, 1 Drawing Figure

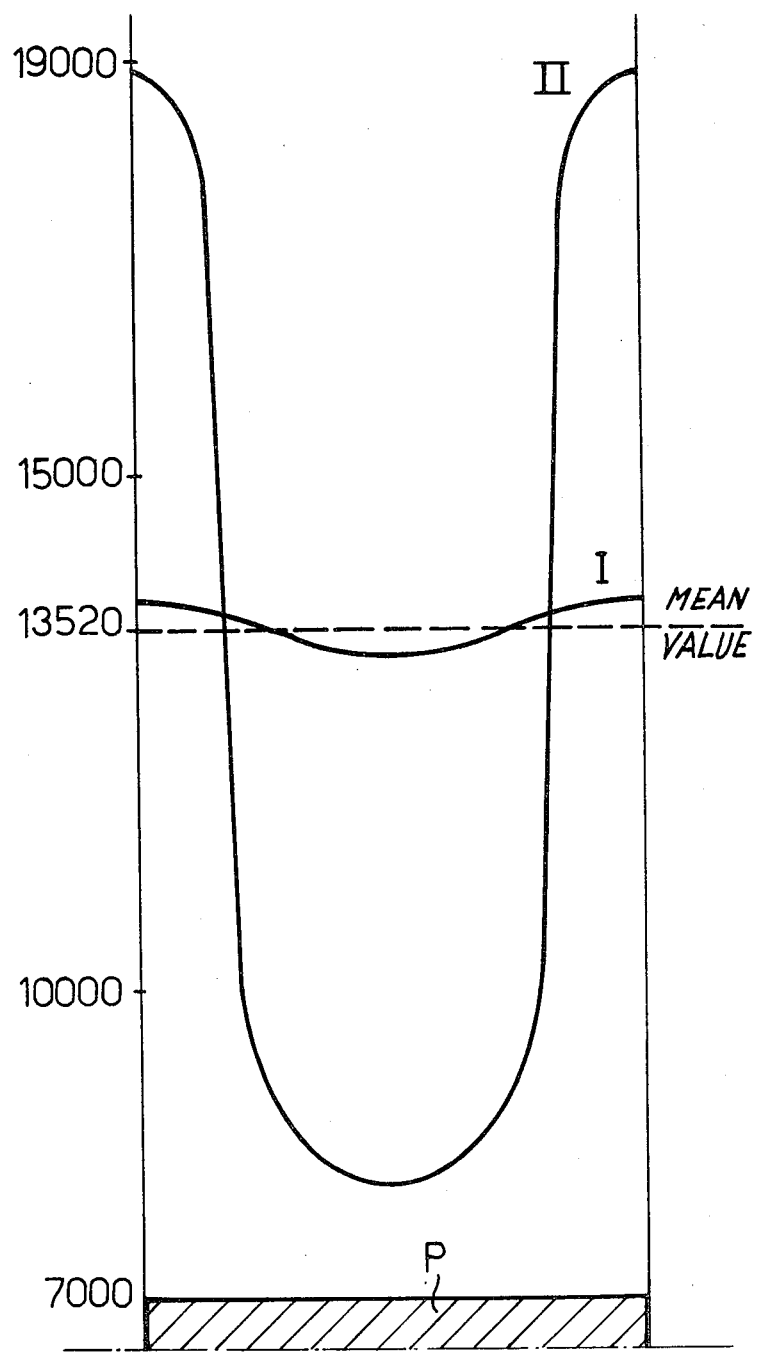

OXYCHLORINATION CATALYST PRECURSOR AND PROCESS FOR ITS PREPARATION

The present invention relates to a catalyst precursor which can easily be activated to transform it into a catalyst which is highly active and selective in the process for the preparation of dichloroethane by the oxychlorination of ethylene. The invention also relates to the process for the oxychlorination of ethylene using the activated catalyst precursor.

The chlorination of gaseous hydrocarbons by means of hydrogen chloride and air, or oxygen, is a process which is well known in the art. In order to accelerate the chlorination reaction, catalysts are used which are constituted by salts, particularly halides, of metals of variable valence, particularly cupric chloride.

These salts, which may be used alone, or in combination with other promoters, are supported on mineral substances such as asbestos, diatomaceous earth, pumice, clay, kieselguhr, alumina, silica and the like. A catalyst which is particularly effective comprises a copper halide, particularly copper chloride, deposited on alumina. The process for chlorinating hydrocarbons is generally carried out by passing a gaseous mixture containing hydrogen chloride, air (or oxygen) and the hydrocarbon through a reaction chamber containing a stationary or fixed bed of the catalyst. More recently the catalyst has been used in finely divided form, in accordance with the art relating to fluidized beds.

The disadvantages of catalysts containing copper halides are described in U.S. Pat. No. 3,010,913, column 1, lines 36 to 46. According to this specification, the greatest disadvantage lies in the volatility of copper halides at the temperature of the oxychlorination. This results in the catalyst being incapable of maintaining its activity over prolonged periods of time due to the loss of the copper halide which must continuously be replaced or recovered and recycled to the reaction zone. This problem of loss of activity is further aggravated when the catalyst is used in the fluidized form. In fact, because of the greater surface area of the catalyst particles, the loss of copper halide is more pronounced and consequently the catalyst has a shorter lifetime.

Attempts have been made to reduce the volatility of copper chloride by combining this salt with an alkali, alkaline earth or other metal chloride (as described for example, in U.K. Pat. No. 969,937). Catalysts have also been described in which the catalytically active part (copper chloride and sodium and/or potassium chloride) is localized in the form of "spots" on a solid granular support (U.S. Pat. No. 3,232,889).

It is found, however, that high local concentrations of catalytic salt, particularly on the outer surface of the support, give rise to a zone of excessively high activity during the oxychlorination in which temperatures at which the catalytic salt fuses are reached. Consequently, when a fluidized catalyst is used, aggregation phenomena occur which slow the movement of the catalyst particles and result in heat exchange problems which worsen with time. Moreover, the addition of components other than copper chloride make the catalyst more complex and only partially resolve the problems related to the volatility of the copper chloride. Such complex catalysts often have values of the activity and selectivity towards the oxychlorination reaction which are less than those of copper chloride alone.

As is known, alumina supports with a high surface area facilitate the reaction between hydrocarbons and oxygen, causing the hydrocarbons to burn. In other words the alumina support is not catalytically inert. When alumina is used as the support in processes in which hydrocarbons and oxygen are present, as is the case in oxychlorination reactions, the fact that alumina is not an inert support cannot be ignored, in that its catalytic activity towards the reaction between the hydrocarbons and oxygen reduces the yield of the desired reaction products. Thus, according to U.K. Pat. No. 1,483,439, alumina in the eta crystallographic form, with a very high surface area (up to 400 $m^2/g$) is used as the support for the oxychlorination catalyst, the support being impregnated with cupric chloride so as not to leave any part of the outer surface of the alumina particles free.

The impregnation process of the U.K. cited Patent involves the "envelopping" of the alumina particles with the copper salt whereby the density of this salt is much greater on the outer surface, and in the parts immediately underlying it, than on the internal surfaces of the particles. The catalysts thus obtained are used in the oxychlorination of ethylene, with high yields of dichloroethane, given the substantial absence of combustion of the ethylene in that contact between the hydrocarbon and the support is practically prevented.

Such catalysts, with high surface densities of copper, have, however, disadvantages relative to their fluidization in that agglomeration of the particles and instability of the fluidized catalytic bed occur.

It may be confirmed that the basic problem relative to catalysts constituted on the one hand by a support part with its own catalytic activity and on the other hand by the catalytically active part proper, lies in distributing the active part on the support part as homogeneously as possible so that the support has hardly any contact with the hydrocarbon. Porous alumina particles which constitute the preferred support for oxychlorination catalysts are characterized in that they have a very large surface area and this surface area is distributed uniformly throughout the entire mass of the particles. Thus, in conclusion the technical problem in the preparation of an active catalyst which uses alumina as the support lies in the distribution of the copper salt within the support with the same uniformity as of the surface of the support itself.

It has now been found that by distributing the copper salt in a uniform and controlled manner over the entire surface of the porous microspheroidal alumina particles catalyst precursors are obtained which can be activated to produce oxychlorination catalysts for ethylene with characteristics which are superior to those of oxychlorination catalysts of the known art, thus solving both the problems relative to the activity and selectivity of the said catalysts and those relative to their fluidization under the oxychlorination conditions.

Known catalysts which have a high density of the copper salt on the outer surface and in the immediately underlying layers of the particles of the support are subject to phenomena of aggregation of the particles probably as a result of fusion of the superficial copper salt. This results in difficulties in operating the fluidized bed given the formation of bubbles, layers, etc. which render the conditions under which the catalyst is activated in the stage preceding the oxychlorination itself critical. The fluidized bed is also unstable during the oxychlorination of the ethylene.

When the porous microspheroidal alumina particles have specific proportions of copper salt uniformly distributed over their entire surface area, the problems relative to the criticality of the conditions of activation of the catalyst are obviated and conditions of stability of the fluidized bed are achieved both in the activation stage and in the ethylene oxychlorination stage. This gives the added advantage of allowing the catalyst precursor to be prepared in separate, specialized apparatus and of allowing the precursor to be activated in an industrial unit without critical conditions.

Accordingly, an object of the present invention is to provide a precursor for a catalyst for the oxychlorination of ethylene, which is free or substantially free from the disadvantages described above.

A further object of the invention is to provide a process for the preparation of the said catalyst precursor.

Yet a further object of the invention is to provide a process for the preparation of dichloroethane by means of the oxychlorination of ethylene, which uses the activated catalyst precursor.

Other objects of the invention will become clear from the following description.

In particular the oxychlorination catalyst precursor of the present invention is constituted by porous microspheroidal alumina particles impregnated with from 3 to 7% by weight of cupric chloride (expressed in terms of the copper metal), the said precursor further being characterized in that it contains from 0.8 to 2.0% by weight of water and in that the copper is uniformly distributed over the entire surface area of the particles, with a degree of non-uniformity of no more than ±7%.

Alumina which is useful as the support preferably has the following characteristics:
porous microspheroidal particles with an average diameter of from 30 to 50 microns; absence of particles larger than 100 to 110 microns; not more than 5 to 10% of the particles smaller than 20 microns;
loss of weight on heating to 900° C. greater than 8%;
surface area: from 120 to 220 m$^2$/g;
pore volume: from 0.35 to 0.5 ml/g;
average radius of the pores: from 30 to 38 Angstroms.
In the preferred embodiment the alumina used as the support has characteristics within the following ranges of values:
surface area: from 140 to 200 m$^2$/g;
pore volume from 0.38 to 0.45 ml/g;
average radius of the pores of the order of 34 to 35 Angstroms.
Preferably the silica content in the alumina used should be less than 0.1%, the iron content should not be greater than 0.03% and the Na$_2$O content should not be greater than 0.01% by weight.

The problem of distributing the copper salt on the porous particles of the support has been confronted many times in the art. Thus U.S. Pat. No. 3,461,084 proposes that anhydrous cupric chloride be mixed under dry conditions with activated alumina which has a weight loss of from 3 to 8% when heated to 1000° C. According to U.S. Pat. No. 2,865,868 the fluidized support particles are impregnated with a solution of the catalytic salt at a temperature below the boiling point of the solution and under conditions such as to avoid the accumulation of the solution itself on the fluidized particles so as to avoid their agglomeration. According to U.S. Pat. No. 3,483,136 the particles impregnated with the catalytic salt are treated with solvent in order to improve the distribution of the salt among the particles.

The expedients described in these Patents certainly give a better distribution of the catalytic salt among the particles subjected to impregnation; they do not, however, enable a uniform distribution of the salt on the individual particles, that is, over their entire surface area, to be achieved.

It has now been found possible to distribute the copper chloride uniformly over the entire surface area of the alumina when the alumina is in the form of porous microspheroidal particles with the characteristics indicated above and when the following expedients are adopted in the impregnation of the particles with the aqueous cupric chloride solution and in the drying of the particles thus impregnated:
impregnation of the fluidized alumina particles at a temperature not greater than 50° C. with an aqueous cupric chloride solution having a CuCl$_2$ concentration of from 16 to 60 g per 100 ml of impregnating solution;
use of a volume of impregnating solution at most equal to 90% of the total pore volume of the alumina;
evaporation of the aqueous solvent from the fluidized particles thus impregnated, by applying a temperature gradient to the fluidizing gas equal to or less than 30 C. degrees/hour, starting from the impregnation temperature up to a maximum of 140° C. followed by heating at this maximum temperature for 0.5 to 15 hours under fluidization conditions.

The conditions under which the aqueous solvent is evaporated from the impregnated particles has been shown to be particularly critical. It is believed that this stage of the process has a decisive influence on the distribution of the copper over the surface of the alumina particles.

Commercial aluminas often contain adsorbed water which is suitably eliminated before the impregnation with the cupric chloride solution. Thus it may be necessary to carry out a pre-treatment at a temperature of from 250° to 500° C. for a time of from 1 to 5 hours, preferably at 300° to 430° C. for a time of from 2 to 3.5 hours. It has been found experimentally that a thermal pre-treatment, when carried out under the conditions indicated above, has a favorable effect on characteristics of the alumina, probably as a result of changes in the number and/or degree of acidity of the hydroxyl groups present in the alumina itself. According to a generally accepted theory, these hydroxyl groups would interact with the deposited copper chloride giving rise to compounds of a different nature and composition.

In the preparation of the catalyst precursor, cupric chloride is used in the anhydrous or hydrated (for example cupric chloride dihydrate) state with a small cationic impurity content (for example iron) of less than 2% by weight and anionic impurity content (for example nitrates) of less than 0.5% by weight.

The solution for impregnating the support is prepared by dissolving cupric chloride in water and the alumina particles are impregnated with the solution obtained while in the fluidized state.

A critical aspect of the process of the present invention is the use of a volume of cupric chloride solution equal to at most 90% of the total pore volume of the support. Thus, for example, in the case of alumina with a pore volume of 0.35 ml/g, the maximum volume of solution usable is about 315 ml/kg of alumina, while in the case of alumina with a pore volume of 0.5 ml/g the maximum volume of solution usable is about 450 ml/kg of alumina.

In the preferred embodiment, a volume of solution equal to 0.7 to 0.9 times the total pore volume of the alumina is used. Obviously the volume of solution which it is intended to use per unit weight of alumina and the quantity of copper desired in the final catalyst (generally from 3 to 7% by weight in terms of the copper metal) is achieved by specifying the concentration of the cupric chloride in the impregnating solution. Under the conditions described above, the concentration of copper chloride in the aqueous solution may vary within a range of from 16 to 60 g of $CuCl_2$ per 100 ml of impregnating solution.

A further critical aspect of the present invention is to impregnate the support while preventing, in this stage, the impregnating solution from becoming saturated with the cupric chloride at the temperature of impregnation.

In practice, the cupric chloride solution is poured gradually on to the alumina particles which are maintained in the fluidized state by means of a flow of gas (air, nitrogen or oxygen).

In order to minimize the evaporation of the solvent this is carried out at low temperatures, for example at ambient temperatures (20° to 25° C.) or below, or at temperatures slightly greater than ambient and up to a maximum of the order of 40° C. to 50° C. By this method good homogenization of the alumina particles with the impregnating solution is achieved.

The impregnated alumina is then subjected to a heat treatment to evaporate the solvent according to the cycle mentioned above. In practice, the fluidizing gas is heated at a temperature gradient of 5 to 40 C. degrees per hour starting from the temperature used for the impregnation, up to a maximum value of 140° C. The fluidized bed is then maintained at the maximum temperature for a period of from 0.5 to 15 hours, preferably 3 to 10 hours, still under fluidizing conditions.

It has been found that, during the drying stage with increasing temperature, the greater part of the water content is removed and the remaining water content at the end of this stage is typically about 2 moles per mole of cupric chloride. During the drying stage at constant temperature, the remaining water content is typically reduced to about 1 mole per mole of cupric chloride. In any case the residual water content in the catalyst precursor finally obtained must be in the range of 0.8 to 2.0% by weight in that, particularly with contents above 2%, the copper distribution in the particles tends to become unstable with time.

It is thought that during the said treatments, interactions occur between the cupric chloride and the hydroxyl groups in the alumina and the following principal reaction has been hypothesized when the reaction is carried out within the range of conditions mentioned previously:

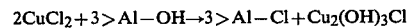

Other possible reactions such as for example:

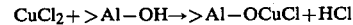

which result in the evolution of gaseous hydrogen chloride instead are undesirable and in practice the evolution of this acid is avoided or at least reduced to negligible values, care being taken not to surpass a temperature of 140° C. in the drying operations. The absence of the evolution of hydrogen chloride, or a slight evolution thereof, constitutes an indication of the proper running of the operation of drying the catalyst precursor.

The catalyst precursor of the present invention contains a quantity of copper (expressed in terms of the metal) of from 3 to 7% by weight, with preferred values of the order of 5% by weight. The values of the surface area and the pore volume of this catalyst depend on those of the alumina chosen as the support and are typically of the order of 5% less than the values for the alumina. From observations by an electron probe, the copper is uniformly dispersed over the entire surface area of the microspheroidal alumina particles with a degree of non-uniformity of no more than ±7%. By the degree of non-uniformity is meant the deviation (expressed as a percentage) of the maximum and minimum values from the arithmetic means of these values.

The precursor is activated by heat in the presence of oxygen, or of a gas containing oxygen (air), at a temperature of the order of 150° to 250° C. In practice this is carried out in the oxychlorination reactor with the catalyst maintained under fluidized conditions by means of an air flow. The activation is generally carried out for a period varying from 4 to 24 hours.

The catalyst activated in this manner is useful in the process for the preparation of dichloroethane by oxychlorination of ethylene. In this process the catalyst is maintained in the fluidized state by means of a gaseous mixture containing ethylene, hydrogen chloride and oxygen. Conveniently air is used as the source of oxygen. The molar ratio of the ethylene to the hydrogen chloride and the oxygen in the feed may be varied generally from 1.01:2.0:0.8 to 1.1:2.0:0.9; however in the preferred embodiment, this reagent ratio is maintained at the following value:

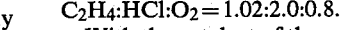

With the catalyst of the present invention it suffices to use a small molar excess only of the ethylene to the hydrogen chloride compared with the stoichiometric value required for the oxychlorination reaction in order to ensure the complete, or substantially complete conversion, of the acid and of the ethylene and thus avoid both the presence of the said acid in the apparatus downstream of the oxychlorination reactor and the high consumption of caustic soda which would otherwise be necessary to absorb the acid from the gases discharged to the atmosphere, and the high loss of ethylene with the waste gases, and finally the atmospheric pollution in which this would result.

The other reaction conditions are: temperature from 200° to 260° C. (preferably 215° to 230° C.), pressure from 2 to 11 atmospheres (preferably from 4 to 8 atmospheres), contact time of from 25 to 45 seconds (preferably from 30 to 40 seconds).

With the catalysts described and with the grain size of the alumina in the size indicated, linear velocities of the fluidizing gas of the order of 30 to 45 cm/sec may be used. Under these conditions the bed has an optimum expansion and good heat exchange properties, with complete absence of phenomena of particle aggregation.

It has in fact been observed, in industrial operations, that the fluidized catalytic bed is practically isothermal, the maximum temperature difference between the various zones being of the order of hardly 1 to 2 C. degrees.

The experimental examples which follow are illustrative and non-limiting of the invention.

The appended drawing is a diagram illustrating the reading of the electron probe on a sample particle of a catalyst precursor.

EXAMPLE 1

A commercial microsperoidal alumina is used having the following characteristics:
average grain size: 40 microns absence of particles larger than 100 microns, 4 to 5% of particles smaller than 20 microns (determination by means of a sedimentation balance)
loss in weight at 900° C.: 8.48% (differential thermal analysis, DTA, by heating from 25° to 900° C. on a thermo-balance with a temperature gradient of 5 C. degrees/min)
surface area: 178 m$^2$/g (B.E.T. determination after degassing for 3 hours at 200° C.)
pore volume: 0.4 ml/g (B.E.T. determination)
average pore radius: 34 Angstroms (B.E.T. determination).

Furthermore the alumina has the indicated impurity content:
$SiO_2$ = 0.08% by weight
Fe = 0.03% by weight
$Na_2O$ = 0.009% by weight.

This alumina is heated in an oven at 380° C. for 3 hours and is then cooled. After this heat treatment the alumina is completely anhydrous and its surface area remains practically unaltered in that a value of 180 m$^2$/g is determined.

The alumina thus treated (800 g) is placed in a glass vessel, of cylindrical form, with an internal diameter of 60 mm, provided with a porous septum at the bottom.

Air is passed through this septum at a rate of about 500 liters/hour so as to ensure a linear velocity of the gas of about 5 cm/sec, good fluidization of the alumina particles being achieved. To one side there are prepared 240 ml of an aqueous solution containing 94.7 g of copper chloride ($CuCl_2$). Thus the volume of the impregnating solution is about 75% of the total pore volume of the alumina.

This solution is dripped from the top of the cylindrical receptacle on to the center of the fluidized bed. Thus drops are prevented from forming on the internal walls of the vessel. The solution is fed uniformly over a period of 40 minutes. The entire operation is carried out at the ambient temperature (25° C.).

At the end of the impregnation, the fluidizing air is heated at a rate of 30 C. degrees per hour, until a maximum temperature of 140° C. is reached.

At this point in the drying, the total quantity of water remaining in the particles is of the order of 25 g as determined by measurement of the quantity of water removed by the fluidizing gas (absorbed in sulphuric acid).

The bed of particles is then maintained under fluidized conditions at 140° C. for a further 6 hours and is then cooled. The quantity of water remaining at the end of the drying treatment is of the order of 12 to 13 g (about 1.4% by weight). Thus a catalyst precursor is obtained with the following characteristics:
copper content (as the metal): 5% by weight (iodometric analysis)
surface area: 170 m$^2$/g.

In order to determine the distribution of the copper over the sufaces of the particles, a determination is carried out with the aid of an electron probe made by the JEOL Company (Model 50/A) as described below.

Particles of the catalyst precursor are embedded in an epoxy resin. The test piece obtained is polished to a finish of 0.25 microns and subsequently metallized with gold. The sample is inserted in the probe and evaluated by observing at least 5 different frames with an enlargement of 1000 times, at least 10 particles being considered for each frame. The images which appear on the monitor are sections of the particles of the catalyst formed during the polishing operation. The measurements effected by the probe relate to points which lie on the scan lines which cut the particle from one side to the other; for each particle, five different diameters are scanned.

The sample hit by the electron beam emits X-rays in proportion to the concentration of copper present at each point scanned and the X-rays are converted into pulses which are counted by a counter in accordance with a scale which has a maximum of 270,000 for a 100% copper concentration and is linearly proportional with 2,700 impulses corresponding to 1% of Cu, 5,400 impulses corresponding to 2% of Cu, and so on.

In the sample examined, the number of pulses varies from a minimum of 13,270, to a maximum of 13,770.

In the drawing, the abscissa represents the diameter of a section of a particle P of the catalyst precursor under examination, while the values of the probe count are given on the ordinate. The curve I represents the values of the probe reading for the catalyst precursor of the present example. Identical curves are obtained by scansion of a further four diameters of the particle under examination.

From the values measured, it is seen that the copper is distributed uniformly over the entire surface area (internal and external) of the particle with a concentration of (13,520/2,700) = 5% by weight and with a degree of non-uniformity of the order of ±2% by weight.

The catalyst precursor thus obtained is placed in a tubular glass reactor, with an internal diameter of 40 mm, provided with a thermocouple at the center and is activated by operating under fluidization conditions with air at 180° C., for 8 hours.

At the end of the activation a gaseous flow is fed to the foot of the reactor and is constituted by:
hydrogen chloride: 278 liters/hour
ethylene: 142 liters/hour
air: 556 liters/hour.

These values are to be understood to be measured at 20° C. and 1 Bar.

The molar ratio of the hydrogen chloride:ethylene:oxygen is thus $HCl:C_2H_4:O_2$ = 2.0:1.02:0.8.

The reaction is carried out at 220° C. at a pressure of 4 Bar and with a contact time of about 30 seconds under the reaction conditions.

The gases from the reaction are subjected to absorption with water, with separation of a liquid phase from a gaseous phase. Both the phases are subjected to gas-chromatographic analysis and the following values of the conversion and activity are obtained, the percentages being expressed in moles:
ethylene conversion: 99.8%
selectivity towards dichloroethane (DCE) with respect to the ethylene converted: 98.5%
conversion of the hydrogen chloride: 99.1%
selectivity towards dichloroethane with respect to the hydrogen chloride converted: 99.7%
behavior of the catalyst under fluidization: the fluidized bed has an optimum behavior, with complete absence of gas bubbles and agglomeration of the particles.

The expansion of the bed is considerable with a bed density which is very low (of the order of 0.5 kg/liter) even at low fluidization velocities (8 to 9 cm/sec), the gas velocity being determined from the total volume of gas supplied under the reaction conditions and the cross section of the empty reactor.

In Table 1 are given the basic data relative to:
characteristics of the alumina
conditions of preparation of the catalyst precursor
characteristics of the precursor
performance of the catalyst under the oxychlorination conditions after 240 hours of continuous operation.

EXAMPLE 2

This is carried out as in Example 1, the alumina being impregnated with 290 ml of an aqueous solution containing 94.7 g of copper chloride ($CuCl_2$). Thus the ratio between the volume of the solution and the pore volume of the alumina is about 0.9.

Examination of the precursor with the probe shows a uniform distribution of the copper with a degree of non-uniformity of the order of ±6%.

The behavior of the catalyst on fluidization is similar to that of Example 1. Other data are given in Table 1.

EXAMPLE 3 (COMPARISON)

This is carried out as in Example 1, the support being impregnated with 320 ml of an aqueous solution containing 94.7 g of copper chloride ($CuCl_2$). Thus the ratio between the volume of the solution and the pore volume of the alumina is about 1.

Examination of the precursor with the probe shows a degree of non-uniformity of the copper distribution of the order of ±9% with a greater density of the copper in the cortical zone of the particles examined.

With regard to the behavior of the catalyst on fluidization, gas bubbles form and the surface of the fluidized bed oscillates. The density of the bed is of the order of 0.6 kg/liter with the velocity of the gas indicated in Example 1.

Other data are given in Table 1.

EXAMPLE 4 (COMPARISON)

This is carried out as in Example 1, the support being impregnation with 385 ml of an aqueous solution containing 94.7 g of copper chloride ($CuCl_2$). Thus the ratio between the volume of the solution and the pore volume of the alumina is about 1.2.

Examination of the precursor with the probe shows a degree of non-uniformity of the copper distribution of ±13%, with a density in the cortical zone of the particles which is higher than that of Example 3.

The behavior of the catalyst under fluidization is unsatisfactory and aggregation of the particles into lumps which gradually break up occurs.

Other data are given in Table 1.

EXAMPLES 5 AND 6

These are carried out as in Example 1, a temperature gradient of 15 C.°/hour and 5 C.°/hour respectively being used during the drying of the catalyst precursor.

Results entirely similar to those of Example 1 are obtained.

EXAMPLE 7 (COMPARISON)

This is carried out as in Example 1, a temperature gradient of 50 C.°/hour being applied during the drying of the catalyst precursor.

Under examination of the precursor with the probe, a degree of non-uniformity of the copper distribution of ±8% is noted, with preferential densification in the cortical zone as in Example 4.

The catalyst exhibits bad fluidization with frequent formation of large gas bubbles in the fluidized bed.

The data are given in Table 1.

EXAMPLE 8 (COMPARISON)

This is carried out as in Example 1, the fluidizing gas being kept at a temperature of 120° C. during the impregnation of the alumina. At the end of the impregnation, the temperature is raised to 140° C. in about 40 minutes and the bed is maintained under these conditions for the subsequent 6 hours.

Examination with the probe shows the precursor obtained to have a degree of non-uniformity of the copper distribution of ±28%.

Curve II in the appended drawing shows the typical readings of the probe. From this curve it is noted that there is strong densification of the copper in the cortical zone of the particle.

The catalyst exhibits bad fluidization with frequent formation of large gas bubbles and a tendency of the particles to agglomerate. The data are given in Table 1.

EXAMPLE 9 (COMPARISON)

A commercial microsperoidal alumina is used with the following characteristics:
average grain size: 37.5 microns absence of particles larger than 100 microns, 5 to 6% of particles smaller than 20 microns
loss of weight at 900° C.: 6.9%
surface area: 250 $m^2/g$
pore volume: 0.3 ml/g
average radius of the pores: 24 Angstroms.

The alumina is heated in an oven to 380° C. for 3 hours and then 800 g of the treated alumina are impregnated with 180 ml of an aqueous solution containing 94.7 g of copper chloride ($CuCl_2$).

The impregnation and subsequent treatments are carried out as described in Example 1, a catalyst precursor and a catalyst having the characteristics and behavior given in Table 1 being obtained.

From the data in Table 1 it is seen that the catalyst obtained has poor values of the selectivity towards dichloroethane both with respect to the ethylene and with respect to the hydrogen chloride converted during the oxychlorination.

EXAMPLE 10 (COMPARISON)

A commercial microspheroidal alumina is used with the following characteristics:
average grain size: 35 microns, absence of particles larger than 100 microns, 7 to 8% of particles smaller than 20 microns
loss of weight at 900° C.: 3.5%
surface area: 150 $m^2/g$
pore volume: 0.6 ml/g
average radius of the pores: 80 Angstroms.

The alumina is heated in an oven at 380° C. for 3 hours and then 800 g of the treated alumina are impregnated with 360 ml of an aqueous solution containing 94.7 g of copper chloride ($CuCl_2$).

The impregnation and subsequent treatments are carried out as described in Example 1, a catalyst precursor and a catalyst being obtained with characteristics and behavior as given in Table 1.

From the data in Table 1 it is seen that the catalyst obtained gives a conversion of the ethylene and of the hydrogen chloride supplied to the oxychlorination reactor which is clearly less than that obtained with the catalysts of Example 1 and 2 although giving a fair selectivity.

In Table 1 only Examples 1 and 2 are carried out with catalysts obtained from precursors according to the present invention while all the other examples serve as comparisons, not having copper distributions within the limits of the invention.

By comparing the conversion yields and selectivities of Examples 1 and 2 with those of Example 7 (which is that with the best yield among the comparison examples) it may easily be calculated that the catalysts obtained from the precursors according to the present invention achieve a saving of from 140 to 448 tons of ethylene/year and a saving of 1314 to 1533 tons of HCl/year (for a plant which produces 100,000 tons/year of dichloroethane).

Furthermore a quantity of alkali of from 1440 to 1680 tons per year is saved (expressed as NaOH at 100%). Consequently, environmental pollution is also drastically reduced.

TABLE 1

| | Ex. 1 | Ex. 2 | Ex. 3 | Ex. 4 | Ex. 7 | Ex. 8 | Ex. 9 | Ex. 10 |
|---|---|---|---|---|---|---|---|---|
| Alumina characteristics | | | | | | | | |
| Average grain size (micron) | 40 | 40 | 40 | 40 | 40 | 40 | 37.5 | 35 |
| Loss in weight at 900° C. (%) | 8.48 | 8.48 | 8.48 | 8.48 | 8.48 | 8.48 | 6.90 | 3.5 |
| Surface area ($m^2$/g.) | 178 | 178 | 178 | 178 | 178 | 178 | 250 | 150 |
| Pore Volume (ml/g.) | 0.4 | 0.4 | 0.4 | 0.4 | 0.4 | 0.4 | 0.3 | 0.6 |
| Average pore radius (Angstrom) | 34 | 34 | 34 | 34 | 34 | 34 | 24 | 80 |
| Precursor preparation | | | | | | | | |
| Solution volume/pore volume ratio | 0.75 | 0.9 | 1 | 1.2 | 0.75 | 0.75 | 0.75 | 0.75 |
| Impregnation temp. (°C.) | 25 | 25 | 25 | 25 | 25 | 120 | 25 | 25 |
| Drying temp. gradient (°C./hour) | 30 | 30 | 30 | 30 | 50 | 30 | 30 | 30 |
| Precursor characteristics | | | | | | | | |
| Copper (metal) (% by weight) | 5 | 5 | 5 | 5 | 5 | 5 | 5 | 5 |
| $H_2O$ content (% by weight) | ~1.4 | ~1.4 | ~1.4 | ~1.4 | ~1.3 | ~0.6 | ~1.4 | ~1.4 |
| Degree of non-uniformity of copper distribution (%) | ±2 | ±6 | ±9 | ±13 | ±8 | ±28 | ±10,5 | ±12 |
| Catalyst behaviour | | | | | | | | |
| Ethylene conversion | 99.8 | 99.25 | 98.6 | 95.5 | 99.0 | 94.7 | 98.1 | 97.0 |
| DCE selectivity | 98.5 | 98.0 | 97.0 | 97.5 | 97.8 | 96.4 | 95.0 | 97.9 |
| HCl conversion | 99.1 | 99.0 | 98.7 | 98.5 | 99.0 | 97.0 | 99.0 | 98.0 |
| DCE selectivity | 99.7 | 99.5 | 97.6 | 98.0 | 97.8 | 96.0 | 97.1 | 97.3 |

We claim:

1. Oxychlorination catalyst precursor constituted by porous microspheroidal alumina particles impregnated with cupric chloride, characterized in that: the cupric chloride content is from 3 to 7% by weight (expressed in terms of copper metal); the particles have a water content of from 0.5 to 2% by weight; and the copper is uniformly distributed over the entire surface area of each particle, with a degree of non-uniformity of not more than ±7%.

2. Precursor according to claim 1, characterized in that the porous microspheroidal alumina particles have the following characteristics:
   average diameter of from 30 to 50 microns;
   absence of particles larger than 100 to 110 microns;
   not more than 5 to 10% of the particles smaller than 20 microns;
   loss of weight through heating to 900° C. greater than 8%;
   surface area from 120 to 220 $m^2$/g;
   pore volume from 0.35 to 0.50 ml/g;
   average pore radius from 30 to 38 Angstroms.

3. Precursor according to claim 2, characterized in that the said alumina particles have the following characteristics:
   surface area from 140 to 200 $m^2$/g;
   pore volume from 0.38 to 0.45 ml/g;
   average pore radius of 34 to 35 Angstroms.

4. Precursor according to claim 1, characterized in that the cupric chloride content is 5% by weight (expressed in terms of the copper metal) and the water content is 1.4% by weight.

5. Process for the preparation of the precursor according to claim 1, characterized by the operations of:
   treating the porous microspheroidal alumina particles thermally by heating them to 250° to 500° C. for a period of from 1 to 5 hours;
   bringing the treated particles to the conditions of a fluid bed by means of a gas maintained at a temperature of not more than 50° C.;
   impregnating the particles in the fluid bed with a volume of from 0.7 to 0.9 times the total pore volume of the particles of an aqueous cupric chloride solution containing from 16 to 60 g of $CuCl_2$ per 100 ml of solution;
   at the end of the impregnation, heating the fluidizing gas with a temperature gradient of from 5 to 30 C. degrees/hour up to a temperature of 140° C. and maintaining this temperature for a period of from 0.5 to 15 hours;
   cooling and recovering the treated particles.

* * * * *